(12) United States Patent
Pillai

(10) Patent No.: US 9,623,217 B2
(45) Date of Patent: Apr. 18, 2017

(54) TRANSVASCULAR ACCESS METHODS

(71) Applicant: Vascular Access Technologies, Inc., Morgantown, WV (US)

(72) Inventor: Lakshmikumar Pillai, Morgantown, WV (US)

(73) Assignee: VASCULAR ACCESS TECHONLOGIES, INC., Morgantown, WV (US)

( * ) Notice: Subject to any disclaimer, the term of this patent is extended or adjusted under 35 U.S.C. 154(b) by 901 days.

(21) Appl. No.: 13/904,876

(22) Filed: May 29, 2013

(65) Prior Publication Data
US 2013/0324901 A1 Dec. 5, 2013

Related U.S. Application Data

(60) Provisional application No. 61/653,303, filed on May 30, 2012.

(51) Int. Cl.
| | | |
|---|---|---|
| *A61M 27/00* | (2006.01) | |
| *A61M 1/36* | (2006.01) | |
| *A61M 25/06* | (2006.01) | |
| *A61B 17/11* | (2006.01) | |

(52) U.S. Cl.
CPC .... *A61M 27/002* (2013.01); *A61B 2017/1107* (2013.01); *A61B 2017/1139* (2013.01); *A61M 1/3653* (2013.01); *A61M 1/3655* (2013.01); *A61M 25/0606* (2013.01)

(58) Field of Classification Search
CPC .............. A61M 1/3655; A61M 27/002; A61M 1/3653; A61M 25/0606; A61B 2017/1107; A61B 2017/1139
See application file for complete search history.

(56) References Cited

U.S. PATENT DOCUMENTS

| | | |
|---|---|---|
| 4,559,039 A | 12/1985 | Ash et al. |
| 4,790,825 A | 12/1988 | Bernstein et al. |
| 4,966,163 A | 10/1990 | Kraus et al. |
| 5,421,348 A | 6/1995 | Larnard |
| 5,492,530 A | 2/1996 | Fischell et al. |
| 5,685,820 A | 11/1997 | Riek et al. |

(Continued)

FOREIGN PATENT DOCUMENTS

| | | |
|---|---|---|
| WO | WO 2004/018029 A2 | 3/2004 |
| WO | WO 2005/053547 A2 | 6/2005 |

(Continued)

OTHER PUBLICATIONS

Faul et al.; Vascular Disease Management; vol. 5; No. 5; pp. 128-133; Sep./Oct. 2008.

(Continued)

*Primary Examiner* — Theodore Stigell
(74) *Attorney, Agent, or Firm* — Shay Glenn LLP

(57) ABSTRACT

Various methods employing transvascular access devices are described, including a method of placing a central catheter in a peripheral vein in an arm of a patient; a method of providing percutaneous access to the heart of a patient; a method of clearing a clotted arteriovenous dialysis graft; a method of creating multiple access points into a single blood vessel; a method of creating an AV fistula in a patient; and a method of providing a bypass to a blockage in a popliteal artery in a patient.

2 Claims, 4 Drawing Sheets

(56) References Cited

U.S. PATENT DOCUMENTS

| | | |
|---|---|---|
| 5,733,248 A | 3/1998 | Adams et al. |
| 6,047,700 A | 4/2000 | Eggers et al. |
| 6,102,926 A | 8/2000 | Tartaglia et al. |
| 6,190,353 B1 * | 2/2001 | Makower ............. A61B 1/3137 600/137 |
| 6,217,527 B1 | 4/2001 | Selmon et al. |
| 6,475,226 B1 | 11/2002 | Belef et al. |
| 6,508,777 B1 | 1/2003 | Macoviak et al. |
| 6,554,794 B1 | 4/2003 | Mueller et al. |
| 6,623,480 B1 | 9/2003 | Kuo et al. |
| 6,726,677 B1 | 4/2004 | Flaherty et al. |
| 6,955,657 B1 | 10/2005 | Webler |
| 7,008,979 B2 | 3/2006 | Schottman et al. |
| 7,374,567 B2 | 5/2008 | Heuser |
| 7,648,517 B2 | 1/2010 | Makower et al. |
| 8,019,420 B2 | 9/2011 | Hine et al. |
| 8,241,311 B2 | 8/2012 | Ward et al. |
| 8,374,680 B2 | 2/2013 | Thompson |
| 8,409,236 B2 | 4/2013 | Pillai |
| 2001/0012924 A1 | 8/2001 | Milo et al. |
| 2001/0023346 A1 | 9/2001 | Loeb |
| 2002/0004666 A1 | 1/2002 | Schwager et al. |
| 2002/0029060 A1 | 3/2002 | Hogendijk et al. |
| 2002/0120250 A1 | 8/2002 | Altman |
| 2002/0133168 A1 | 9/2002 | Smedley et al. |
| 2002/0169377 A1 | 11/2002 | Khairkhahan et al. |
| 2004/0039371 A1 | 2/2004 | Tockman et al. |
| 2004/0059280 A1 | 3/2004 | Makower et al. |
| 2004/0082850 A1 | 4/2004 | Bonner et al. |
| 2004/0133168 A1 | 7/2004 | Salcudean et al. |
| 2004/0181150 A1 | 9/2004 | Evans et al. |
| 2004/0181238 A1 | 9/2004 | Zarbatany et al. |
| 2005/0101984 A1 | 5/2005 | Chanduszko et al. |
| 2005/0149097 A1 | 7/2005 | Regnell et al. |
| 2005/0209579 A1 | 9/2005 | Yacoubian et al. |
| 2006/0009737 A1 | 1/2006 | Whiting et al. |
| 2006/0135962 A1 | 6/2006 | Kick et al. |
| 2006/0247750 A1 | 11/2006 | Seifert et al. |
| 2007/0021767 A1 | 1/2007 | Breznock |
| 2007/0203515 A1 * | 8/2007 | Heuser ................... A61B 17/11 606/184 |
| 2008/0082136 A1 | 4/2008 | Gaudiani |
| 2008/0125748 A1 | 5/2008 | Patel |
| 2008/0154172 A1 | 6/2008 | Mauch |
| 2008/0215008 A1 | 9/2008 | Nance et al. |
| 2008/0249565 A1 | 10/2008 | Michler et al. |
| 2009/0112050 A1 | 4/2009 | Farnan et al. |
| 2009/0240122 A1 | 9/2009 | Avitsian |
| 2010/0249491 A1 | 9/2010 | Farnan et al. |
| 2011/0178530 A1 | 7/2011 | Bly |
| 2011/0295206 A1 | 12/2011 | Gurley |
| 2012/0136247 A1 | 5/2012 | Pillai |
| 2012/0136366 A1 | 5/2012 | Pillai et al. |
| 2013/0006282 A1 | 1/2013 | Wilkinson |
| 2013/0172922 A1 | 7/2013 | Pillai et al. |
| 2014/0142418 A1 | 5/2014 | Gurley et al. |

FOREIGN PATENT DOCUMENTS

| | | |
|---|---|---|
| WO | WO 2011/068540 A1 | 6/2011 |
| WO | WO 2013/119547 A1 | 8/2013 |

OTHER PUBLICATIONS

Huang et al.; Evaluation of the needle technique for producing an arteriovenous fistula; Journal of Applied Physiology; vol. 77(6); pp. 2907-2911; Dec. 1994.

Khanna et al.; Sharpening of hollow silicon microneedles to reduce skin penetration force; J. Micromech. Microeng.; vol. 20; No. 4, pp. 045011 (8 pgs.); Mar. 15, 2010.

LuMEND, Inc.; Outback LTD re-entry catheter; Product Resources (http://www.lumend.com/Images/Technology/Product/brochure. pdf) This web address was available to applicant(s) at least as of (Jul. 19, 2006).

Mewissen, Mark; Revascularization of long FP arterial occlusions; Endovascular Today; pp. 2-4; Mar. 2004.

O'Callaghan et al.; Dynamics of stab wounds: force required for penetration of various cadaveric human tissues; Forensic Sci. Int'l; vol. 104; pp. 173-178; Oct. 11, 1999.

Pillai, Lakshmikumar; U.S. Appl. No. 11/381,229 entitled "Methods of Transvascular Retrograde Access Placement and Devices for Facilitating Therein," filed May 2, 2006.

Pillai et al.; U.S. Appl. No. 13/906,122 entitled "Tranvascular Access Device and Method," filed May 30, 2013.

* cited by examiner

TRANSVASCULAR ACCESS METHODS

CROSS REFERENCE TO RELATED APPLICATIONS

This application claims the benefit of U.S. Application No. 61/653,303, filed May 30, 2012, the disclosure of which is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND

The present invention relates to methods and devices for providing transvascular access to blood vessels. Prior devices and methods have been described for providing, e.g., access for placing a central venous line in the jugular vein using a remote vascular entry point, such as the femoral vein. In those prior approaches, a steerable catheter with a bent or bendable tip is guided from the femoral or other entry point to the desired central venous line entry point in the jugular vein. The tip of a sharp wire or stylet is then advanced out of the catheter and through the vessel wall and skin of the patient, and the central venous line is then inserted over the wire or stylet. More details of these prior devices and methods may be found in U.S. Appl. No. 61/653,182 (filed May 30, 2012); application Ser. No. 12/861,716 (filed Aug. 23, 2010), now U.S. Pat. No. 8,409,236; U.S. application Ser. No. 12/366,517 (filed Feb. 5, 2009); and U.S. application Ser. No. 11/424,131 (filed Jun. 14, 2006), the disclosures of which are incorporated herein by reference.

SUMMARY OF THE DISCLOSURE

The present invention relates to methods for providing transvascular access to intravascular or intracardiac locations.

One aspect of the invention provides a method of placing a central catheter in a peripheral vein in an arm of a patient, such as a cephalic vein, a basilic vein or a brachial vein. The method includes the steps of inserting an access device percutaneously through an entry site in a femoral vein of the patient, the access device comprising a vascular catheter; advancing a distal end of the vascular catheter from the entry site to an exit site in the peripheral vein; advancing a puncture tool from the distal end of the catheter through the peripheral vein wall and skin of the patient at the exit site; and after the step of advancing the puncture tool, inserting the central catheter into the peripheral vein at the exit site.

Another aspect of the invention provides a method of providing percutaneous access to the heart of a patient. The method includes the steps of inserting an access device percutaneously through an entry site in a femoral artery of the patient, the access device comprising a vascular catheter; advancing a distal end of the vascular catheter from the entry site to an exit site in an axillary artery of the patient; advancing a puncture tool from the distal end of the catheter through the axillary artery wall and skin of the patient at the exit site; after the step of advancing the puncture tool, inserting a cardiac access catheter into the axillary artery at the exit site; and advancing the cardiac access catheter through the axillary artery, subclavian artery and the aorta to the patient's heart to, e.g., perform transcatheter aortic valve implantation or implant a left ventricular assist device.

Still another aspect of the invention provides a method of clearing a clotted arteriovenous dialysis graft. The method includes the steps of inserting an access device into the graft at a first access point (e.g., above an arterial anastomosis), the access device comprising a vascular catheter; advancing a distal end of the vascular catheter from the first access point through the graft to a second access point in the graft (e.g., in front of a venous graft anastomosis); advancing a puncture tool from the distal end of the catheter through the graft wall at the second access point; and inserting a clot clearing device into the graft at the second access point.

Another aspect of the invention provides a method of creating multiple access points into a single blood vessel. The method includes the steps of inserting an access device percutaneously into the vessel through a first access point, the access device comprising a vascular catheter; advancing a distal end of the vascular catheter from the first access point through the vessel to a second access point; advancing a puncture tool from the distal end of the catheter through the vessel wall and skin of the patient at the second access point; inserting a catheter or device into the vessel at the second access point; removing the access device from the vessel; and inserting another catheter or device into the vessel at the first access point.

Yet another aspect of the invention provides a method of creating an AV fistula in a patient. The method includes the steps of inserting an access device into the patient's femoral artery, the access device comprising a vascular catheter; advancing a distal end of the vascular catheter to a fistula site within the axillary artery; advancing a puncture tool from the distal end of the catheter through the axillary artery wall into the axillary vein to form a fistula between the axillary artery and the axillary vein; and inserting a covered stent into the fistula. In some embodiments, the method also includes before the step of inserting the covered stent, expanding the size of the fistula. In some embodiments the method also includes the step of inserting an intravascular ultrasound device into the femoral vein and advancing the intravascular ultrasound device to a position in the axillary vein adjacent to the vascular catheter.

Still another aspect of the invention provides a method of providing a bypass to a blockage in a popliteal artery in a patient. The method includes the steps of inserting a first access device into the patient's femoral artery at a first entry point, the first access device comprising a vascular catheter; advancing a distal end of the first access device vascular catheter to a first exit point upstream of the blockage; advancing a puncture tool from the distal end of the first access device vascular catheter through the arterial wall at the first exit point; inserting a second access device into the patient's tibial artery at a second entry point, the second access device comprising a vascular catheter; advancing a distal end of the second access device vascular catheter to a second exit point downstream of the blockage; advancing a puncture tool from the distal end of the second access device vascular catheter through the arterial wall at the second exit point; forming a subcutaneous tunnel between the first exit point and the second exit point; extending a guidewire between the first entry point and the second entry point; and delivering a bypass graft along the guidewire to extend between the first exit point and the second exit point. The some embodiments, the method also includes the step of making an incision through the patient's skin at the first exit point prior to the step of advancing the puncture tool from the distal end of the first access device vascular catheter through the arterial wall at the first exit point.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

The devices and methods described in the patent applications listed above form the basis for improving some existing procedures and for performing entirely new procedures. Some of these medical methods are described below.

Placement of a Peripherally Inserted Central Catheter

Figure 1:
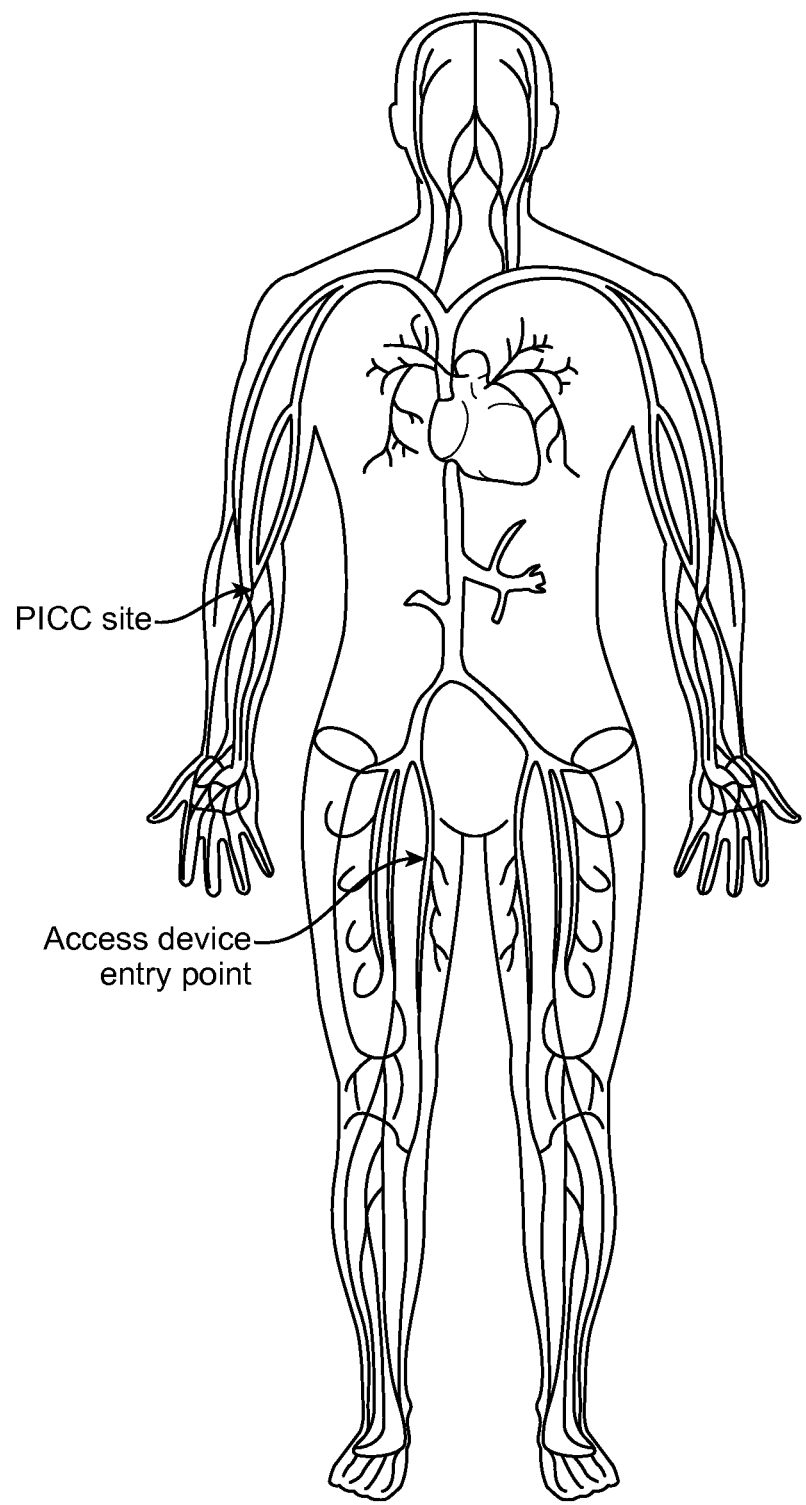
FIG. 1 shows possible entry points for a transvascular access device and a peripherally inserted central catheter according to one method of this invention.

A peripherally inserted central catheter (PICC) is a form of intravenous access typically used for patients who require intravenous delivery of a drug or nutrition over an extended period of time. The devices described in U.S. application Ser. No. 61/653,182; U.S. Pat. No. 8,409,236; U.S. application Ser. Nos. 12/366,517; and 11/424,131 can be used to facilitate placement of a PICC. The device may be inserted as described in these patent applications, then advanced to a site in, e.g., the cephalic vein, basilic vein or brachial vein, and the device's puncture tool (e.g., sharp stylet or needle-tipped guidewire) can be passed through the vein wall and skin to create the PICC entry point, as shown in FIG. 1. After optionally using a micropuncture catheter at the new entry point, the PICC can then be advanced into the vein.

Peripheral Artery Access For Percutaneous Retrograde Access of the Heart

Certain minimally invasive cardiac procedures require retrograde access of the heart. For example, transcatheter aortic valve implantation (TAVI) can be performed using catheters inserted into the axillary artery and advanced to the heart. As another example, left ventricular assist devices can be implanted using catheters inserted into the axillary artery and advanced to the heart.

The invention includes use of devices described in U.S. Appl. No. 61/653,182; U.S. Pat. No. 8,409,236; U.S. application Ser. Nos. 12/366,517; and 11/424,131 to create the arterial access for procedures performed in or around the heart. The device may be inserted into the femoral artery and advanced to the desired entry point in the axillary artery (or other great artery of the head and neck, such as the carotid or subclavian arteries). The device's puncture tool (e.g., sharp stylet or needle-tipped guidewire) can be passed through the arterial wall and skin at an exit site to create the new catheter entry point. After optionally using a micro-puncture catheter at the new entry point, the opening (arteriotomy) can be enlarged to the desired size, and the catheter can then be inserted into the axillary artery and advanced to the heart through the subclavian artery and aorta to perform the desired implant or other procedure. Access directly to a carotid artery or subclavian artery can also be provided in the same manner.

Treatment of Clotted Dialysis AV Graft

Hemodialysis often requires access to an autologous arteriovenous (AV) fistula formed by connecting an artery with a nearby vein. AV grafts are often used for dialysis patients who are not good candidates for an AV fistula. The AV graft is a tube formed from polyester or other biocompatible material that extends from a vein to an artery, often forming a loop in between. An AV graft may be placed, e.g., between the brachial artery and the antecubital vein, between the radial artery and the antecubital vein, between the brachial artery and the axillary vein, or between the axillary artery and the axillary vein.

AV grafts can become occluded by clotted blood. Since there is no blood flow, it can be very difficult to puncture a clotted graft from the outside and place a vascular sheath in the collapsed lumen. The invention therefore includes methods and devices for clearing AV graft clots in, e.g., an upper arm or forearm AV graft.

Figure 2:
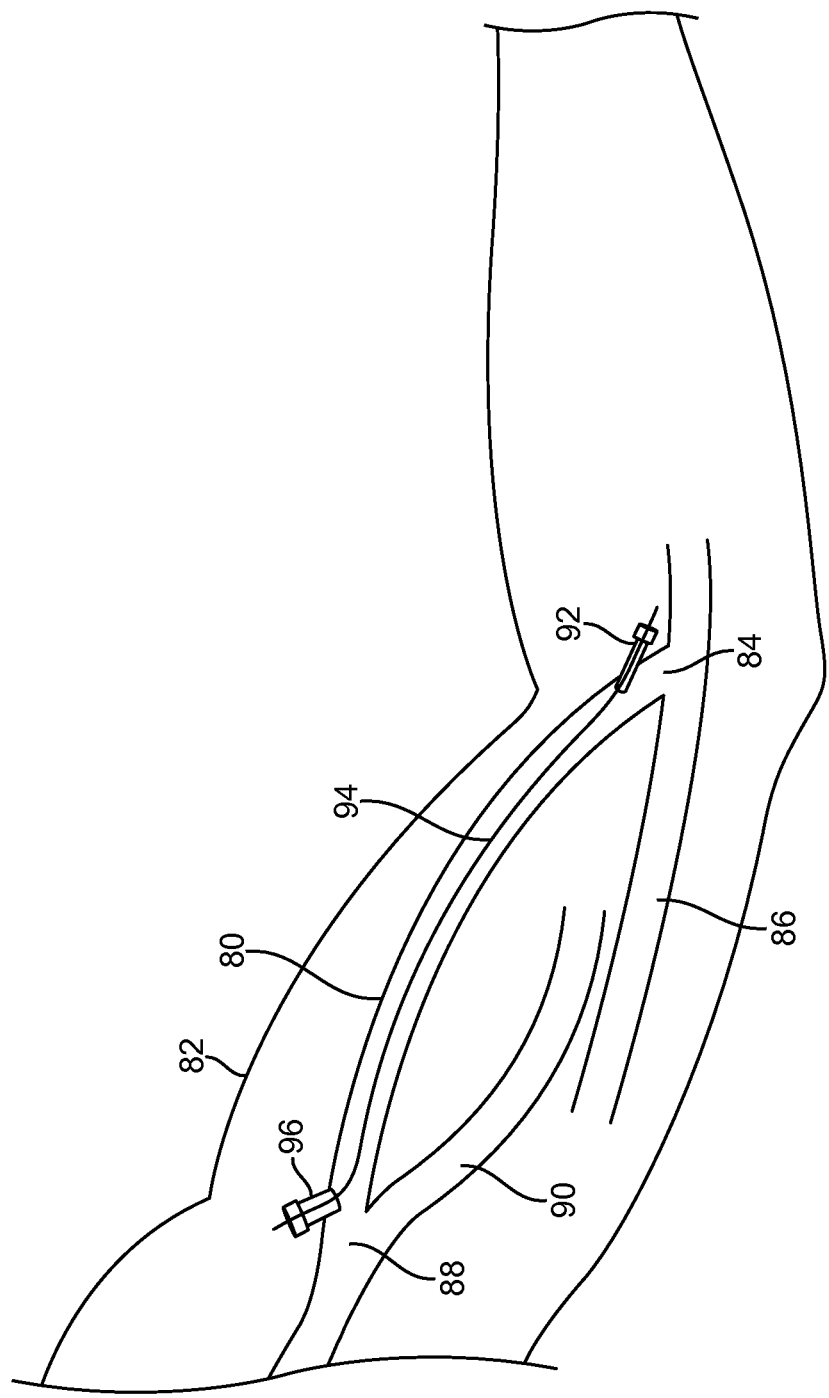
FIG. 2 illustrates a method for clearing a clotted dialysis graft according to an aspect of this invention.

FIG. 2 shows how a vascular access device can be used to clear a clotted dialysis graft. As shown, an AV graft 80 is disposed in the patient's arm 82 extending from an arterial anastomosis 84 in the brachial artery 86 to a venous anastomosis 88 in the axillary vein 90. To clear the clot, the graft 80 can be percutaneously punctured just above its arterial anastomosis 84 with an 18 gauge entry needle aimed toward the venous graft anastomosis 88 and a 6F standard vascular sheath 92 can be inserted. The venous limb and venous anastomosis 88 of the graft 80 can be declotted in the usual fashion with a suction-aspiration device (e.g., AngioJet®), and a balloon angioplasty of the venous anastomosis 88 can be performed. Then, using a device somewhat shorter than that described, e.g., in U.S. Appl. No. 61/653,182; U.S. Pat. No. 8,409,236; U.S. application Ser. Nos. 12/366,517; or 11/424,131, pass the device through the vascular sheath 92 and fire the stylet out of the graft 80 to puncture through the vessel and skin just in front of the venous graft anastomosis 88. The device's stylet may then be retracted and, using a micro-puncture catheter, a 0.035" wire 94 may be inserted into the new opening. A second 6F vascular sheath 96 may then be placed over the wire. Through this new sheath the arterial anastomosis may be re-opened in the usual fashion with the AngioJet® catheter and over the wire Fogarty balloon. The sheaths may now be removed as the graft has now been declotted and is ready for dialysis access. This approach is particularly advantageous when declotting upper arm AV grafts; trying to puncture the graft just below the venous anastomosis (which is usually in the axilla-armpit) can be a challenge ergonomically, especially with the x-ray imager (C-arm) being in the way.

This approach can also be used with other vascular-based procedures requiring multiple openings in a vessel, such as ICD or pacemaker lead placement.

Creation of Multiple Access Openings in a Single Vessel

There are many procedures requiring the creation of multiple entry points into a single blood vessel for, e.g., the insertion of multiple devices into the vessel. For example, Tesio® long term hemodialysis catheters require two openings, one for each of the two free floating lumens. These catheters are typically placed in the jugular vein or subclavian vein approximately 8 mm apart. As another example, up to four electrophysiology catheters may be inserted into adjacent portions of a femoral vein and advanced to the patient's heart for electrophysiology studies or for cardiac ablation procedures. As yet another example, when implanting leads for pacemakers or implantable cardioverter/defibrillators (ICDs), multiple contiguous punctures often need to be made along the access vein (e.g., subclavian vein). Other procedures require multiple punctures and insertions in the same veins or arteries.

Veins can go into spasm after a first puncture, making subsequent punctures difficult. The device described in, e.g., U.S. Appl. No. 61/653,182; U.S. Pat. No. 8,409,236; U.S. application Ser. Nos. 12/366,517; or 11/424,131 can be used to create the second and subsequent openings in the vessel followed by insertion of the second and subsequent catheters. Specifically, the device can be inserted into the first entry point in the vessel, then advanced to the second desired entry point. The device's puncture tool (e.g., sharp stylet or needle-tipped guidewire) can then be passed through the vein wall and skin to create the second entry point. After optionally using a micropuncture catheter at the new entry point, one of the catheters can then be inserted into the vessel at this second entry point while another of the catheters can be inserted at the first entry point after removal of the transvascular device.

Creation of AV Fistula For Hemodialysis

Hemodialysis often requires access to an autologous arterial/venous (AV) fistula formed by connecting an artery with a nearby vein. For example, an anastomosis can be formed between the cephalic vein and the radial artery up near the patient's wrist, between the perforating branch of the cephalic vein and proximal radial artery in the patient's forearm, between the median antecubital vein and proximal radial artery in the patient's forearm, between the brachial artery and cephalic vein further up the patient's arm, etc.

Figure 3:
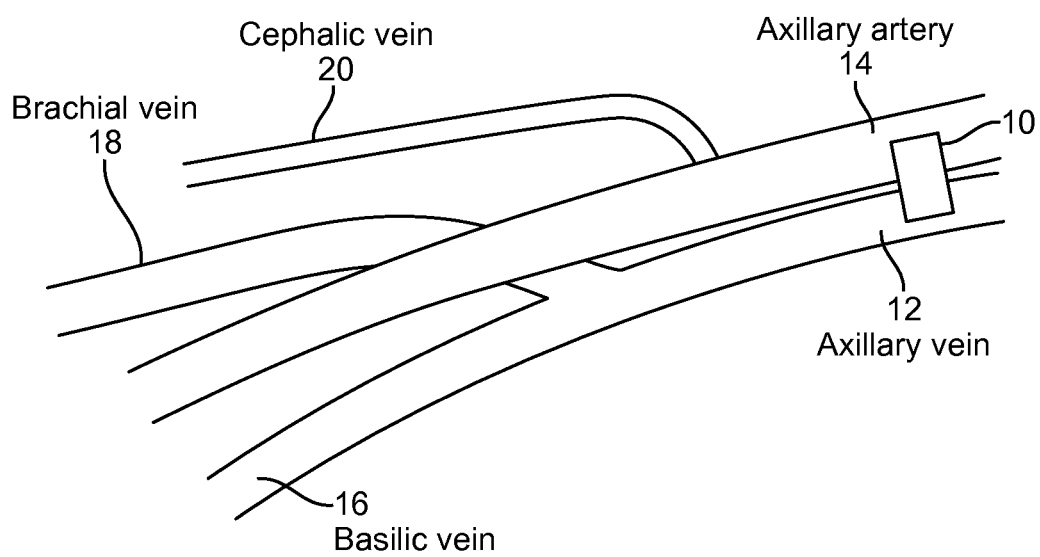
FIG. 3 illustrates creation of an arterial/venous fistula according to an aspect of this invention.

While forearm or upper arm access sites are useful for hemodialysis, AV fistulas in the arm are often not viable for very long due to clotting, fibrosis, etc. As an alternative, the device described in, e.g., U.S. Appl. No. 61/653,182; U.S. Pat. No. 8,409,236; U.S. application Ser. Nos. 12/366,517; or11/424,131 can be used to create a longer lasting fistula remote from the access site. FIG. 3 shows schematically an AV fistula 10 created between the axillary vein 12 and the axillary artery 14. These vessels are disposed adjacent to each near the shoulder. The axillary vein drains the basilic vein 16, the brachial vein 18 and the cephalic vein 20.

To create the fistula 10, a device is inserted percutaneously into the femoral artery advanced over a guidewire to the desired position in the axillary artery. An intravascular ultrasound (IVUS) device is inserted into the femoral vein and advanced to an adjacent position in the axillary vein to monitor positioning of the device in the axillary artery. Once the position is confirmed, the device's puncture tool (e.g., sharp stylet or needle-tipped guidewire) can then be passed through the wall of the axillary artery into the axillary vein.

Thereafter, a 6 mm balloon can be placed through the AV puncture (either from the arterial side or the venous side) and inflated to expand the opening. A 6 mm covered stent can then be placed in the expanded opening to maintain the patency of the fistula. Then, to enable retrograde flow of arterial blood from the fistula in the axillary vein down to a peripheral vein in the arm (e.g., cephalic vein, basilic vein or antecubital vein) for hemodialysis access, a valvulotome is inserted into the desired vein to lyse the valves.

In another embodiment, a magnet or magnets on the devices in the axillary vein and axillary artery can be used to line up the fistula puncture point.

Percutaneous bypass for femoral-popliteal arterial occlusion

Peripheral artery disease can cause blockage of an artery in the leg, such as the popliteal artery. Current procedures include the use of a grafted bypass leading from the femoral artery to a point beyond the blockage.

Figure 4:
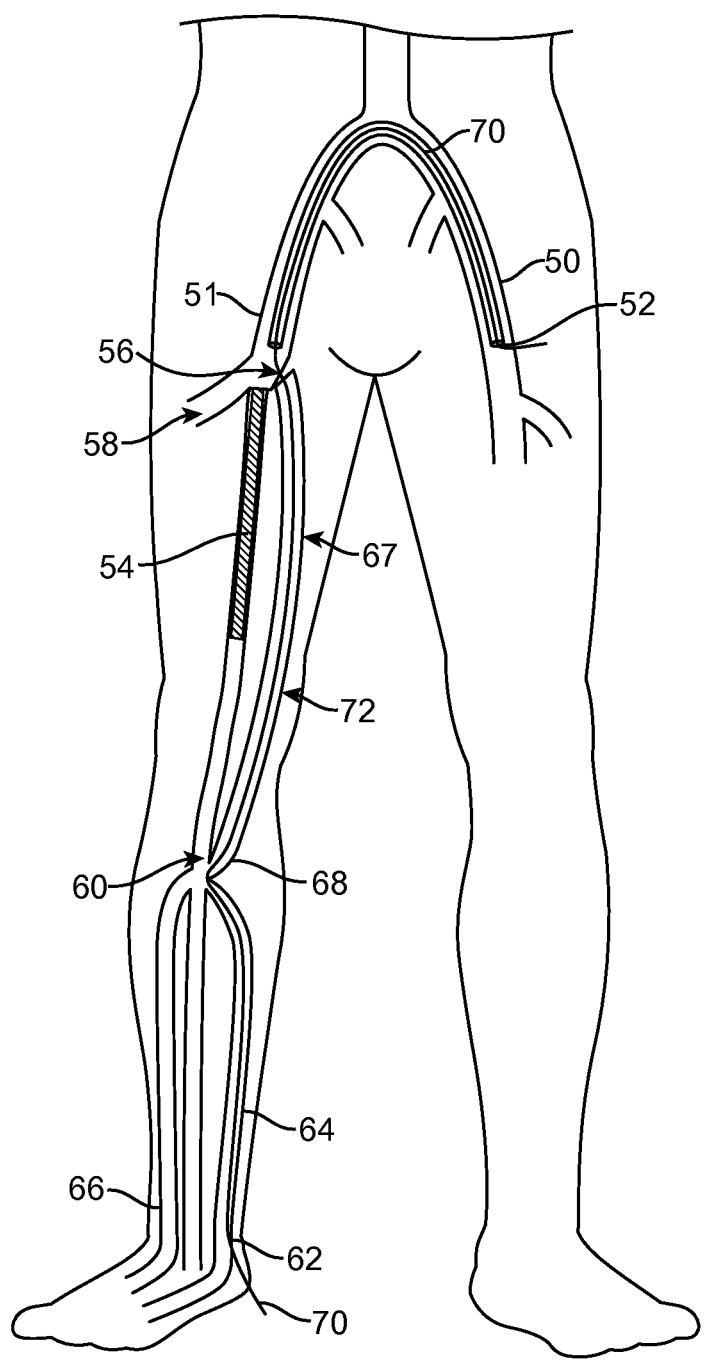
FIG. 4 illustrates placement of a popliteal bypass graft according to an aspect of this invention.

Devices as described in, e.g., U.S. Appl. No. 61/653,182; U.S. Pat. No. 8,409,236; U.S. application Ser. Nos. 12/366, 517; or 11/424,131 can be used to implant a popliteal bypass graft in a less invasive manner. As shown in FIG. 4, to treat a blockage in the patient's right leg, a first device is inserted in a first entry point 52 in the femoral artery 50 in the left leg and advanced through the femoral artery 51 in the right leg to a point just above the blockage 54. In one embodiment, an incision can be made to expose the right femoral artery at the desired exit point 56 (shown here to be near the junction of the profunda femoral artery 58 and the popliteal artery 60), and the device's puncture tool (e.g., sharp stylet or needle-tipped guidewire) can be passed through the femoral artery wall. Alternatively, the device's puncture tool can be passed through the femoral artery wall and skin of the patient at the exit point 56 without first making an incision.

A second device may be inserted at an entry point 62 in the patient's right tibial artery 64 (or, alternatively, the patient's pedal artery 66) and advanced to its desired exit point 68 beyond the blockage point (shown here as near the junction of the popliteal artery and the tibial artery). Once again, an incision can be made to expose the popliteal artery at the exit point 68 prior to passing the device's puncture tool through the arterial wall. Alternatively, the device's puncture tool can be passed through the arterial wall and skin at the exit point 68 without a prior incision.

Next, a subcutaneous tunnel 67 may be formed between two incisions (not shown) at locations 56 and 68. A 260 exchange catheter may be used to facilitate switching of the two guidewires or stylets with a single guidewire 70 extending from entry point 52 to entry point 62 through the subcutaneous tunnel 67. An expandable covered 6 mm stent graft 72 may then be advanced from, e.g., entry point 52 over the guidewire 70 to the subcutaneous tunnel to extend between the femoral artery exit point to the popliteal artery exit point, then expanded to seal the bypass in place.

What is claimed is:

1. A method of providing a bypass to a blockage in a popliteal artery in a patient, the method comprising:
    inserting a first access device into the patient's femoral artery at a first entry point, the first access device comprising a vascular catheter;
    advancing a distal end of the first access device vascular catheter to a first exit point upstream of the blockage;
    advancing a puncture tool from the distal end of the first access device vascular catheter through arterial wall and skin at the first exit point;
    inserting a second access device into the patient's tibial artery at a second entry point, the second access device comprising a vascular catheter;
    advancing a distal end of the second access device vascular catheter to a second exit point downstream of the blockage;
    advancing a puncture tool from the distal end of the second access device vascular catheter through arterial wall and skin at the second exit point;
    forming a subcutaneous tunnel between the first exit point and the second exit point;
    extending a guidewire between the first entry point and the second entry point; and
    delivering a bypass graft along the guidewire to extend through the subcutaneous tunnel between the first exit point and the second exit point.

2. The method of claim 1 further comprising making an incision through the patient's skin at the first exit point prior to the step of advancing the puncture tool from the distal end of the first access device vascular catheter through the arterial wall at the first exit point.

\* \* \* \* \*